(12) United States Patent
Chen (10) Patent No.: US 12,319,908 B1
(45) Date of Patent: *Jun. 3, 2025

(54) SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES

(71) Applicant: University of South Florida, Tampa, FL (US)

(72) Inventor: Wei Chen, Tampa, FL (US)

(73) Assignee: University of South Florida, Tampa, FL (US)

( * ) Notice: Subject to any disclaimer, the term of this patent is extended or adjusted under 35 U.S.C. 154(b) by 617 days.

This patent is subject to a terminal disclaimer.

(21) Appl. No.: 17/697,582

(22) Filed: Mar. 17, 2022

Related U.S. Application Data (60) Provisional application No. 63/162,171, filed on Mar. 17, 2021.

(51) Int. Cl.
*C12N 13/00* (2006.01)
*A61N 1/36* (2006.01)
*C12M 1/42* (2006.01)

(52) U.S. Cl.
CPC .............. *C12N 13/00* (2013.01); *C12M 35/02* (2013.01)

(58) Field of Classification Search
CPC .. A61N 1/36034; A61N 1/0456; H01T 23/00; C12N 13/00; C12M 35/02

USPC ...................................................... 607/71–72
See application file for complete search history.

(56) References Cited

U.S. PATENT DOCUMENTS

| 4,165,750 | A | 8/1979 | Aleev et al. | |
|---|---|---|---|---|
| 8,073,549 | B2 * | 12/2011 | Chen | A61N 1/32 607/2 |
| 12,179,020 | B1 * | 12/2024 | Chen | H01T 23/00 |
| 2009/0054829 | A1 * | 2/2009 | Chen | A61N 1/32 604/20 |
| 2015/0231408 | A1 * | 8/2015 | Williams | A61N 5/06 607/88 |
| 2019/0296521 | A1 * | 9/2019 | Yun | H01S 5/36 |

OTHER PUBLICATIONS

Tran et al. "Synchronization Modulation Increases Transepithelial Potentials in MDCK Monolayers through Na/K Pumps" vol. 8 issue 4 Plos one. Apr. 2013, pp. 1-9.

(Continued)

*Primary Examiner* — Michael J Lau
(74) *Attorney, Agent, or Firm* — Molly L. Sauter; Smith & Hopen, P.A.

(57) ABSTRACT

A system and method for controlling active ion transporters, such as sodium-potassium (Na/K) pumps to actively transports 3 $Na^+$ and 2 $K^+$ ions by consuming one ATP. The system and method provide an oscillating electric field that is effective in running the active ion-transport at their physiological running mode by consuming one ATP molecule to actively transport ion and to synthesize one ATP for each pumping cycle. The ATP molecule that is synthesized compensates for the ATP molecule that is consumed in actively transporting ions, resulting in a net-consumption of ATP that is significantly reduced, theoretically to zero.

18 Claims, 9 Drawing Sheets

(56) References Cited

OTHER PUBLICATIONS

Jeon et al. "Effects of Pulse Duration on Muscle Fatigue Duringelectrical Stimulation Inducing Moderate-Level Contraction" Pulse Duration Effects during NMES,Muscle & Nerve. Apr. 2018, pp. 1-8.
Mckenna et al. "Muscle K+, Na+, and Cl-disturbances and Na+—K+ pump inactivation: implications for fatigue" J Appl Physiol Oct. 2007, pp. 1-8.
Liang, "The modied Synchronization Modulation technique revealed mechanisms of Na,K-ATPase" ProQuest LLC, Mar. 2019. pp. 1-103.
Dreibati et al. "Influence of electrical stimulation frequency on skeletal muscle force and fatigue" Annals of Physical and Rehabilitation Medicine 53 (2010) 266-277, Jan. 2010. pp. 1-12.
Chen et al. "Electrical Activation of Na/K Pumps Can Increase Ionic Concentration Gradient and Membrane Resting Potential" J. Membrane Biol. 214, 147-155 (2007) pp. 1-9.
Liu et al. "Activation of Na+ and K+ Pumping of (Na,K)—ATPase by an Oscillating Electric Field" The journal of Biological Chemistry vol. 265, No. 13, Issue if May 5 pp. 7260-7267, May 1990, pp. 1-9.
Di et al. "Effects of power frequency electric field exposure on kidney" Ecotoxicology and Environmental safely 194 (2020) 110354 Feb. 2020, pp. 1-7.
Blank, "Na, K-ATPase function in alternating electric fields" The FASEB Journal vol. $ Mar. 2020, pp. 1-5.
Taghian et al. "Modulation of cell function by electric field: a high-resolution analysis" 2015 The Author(s) Published by the Royal Society. Apr. 2015, pp. 1-11.

* cited by examiner

SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES

CROSS-REFERENCE TO RELATED APPLICATIONS

This application claims priority to U.S. Provisional Patent Application No. 63/162,171 filed on Mar. 17, 2021, and entitled, "SYSTEM AND METHOD UTILIZING ELECTRICAL ENERGY TO FUEL AND ACTIVATE ACTIVE ION TRANSPORTERS WITHOUT CONSUMPTION OF ADENOSINE TRIPHOSPHATE (ATP) MOLECULES", which is incorporated by reference herein in its entirety.

BACKGROUND OF THE INVENTION

In living systems there are many active ion-transporters, such as electrogenic pump molecules and active ion-exchangers in cell membranes. These active ion-transporters maintain the specific ionic concentrations in the cell as well as the ionic concentration gradients across the cell membrane, wherein ionic concentration gradients result in an electrical potential across the cell membrane. The ionic concentration gradients and the membrane potential constitute electrochemical potential across the cell membrane, which is critical to many cell functions. For example, at rest, about 40% of adenosine triphosphate (ATP) molecules are consumed by sodium-potassium Na/K pumps, one of the most prevalent active ion transporters.

The electrochemical potential is the source for the generation and propagation of the action potential for all the excitable cells, such as nerve cells, skeletal muscle fibers, and cardiac cells. This electrochemical potential also provides energy to many other membrane active transporters, such as the sodium-hydrogen (Na/H) exchangers, that influence pH value. The ionic concentration gradients also play a significant role in controlling the cell volume and homeostasis. Therefore, maintaining the ionic concentration gradients and the membrane potential is critical to living cells.

The Na/K pump, or Na/K ATPase (adenosine triphosphatases) is one of the most prevalent house-keeping proteins found within the membrane of almost every cell. The Na/K pump extrudes three Na ions out of the cell via the exchange of two K ions and consumption of one adenosine 5'-triphosphate (ATP) during each pumping cycle in order to maintain the ionic concentration gradients and the cell membrane potential. The Na/K pump is a unique energy converter which converts ATP hydrolysis energy to the electrochemical potential difference across the cell membrane so that the membrane proteins can easily use the energy.

Many diseases, or non-physiological conditions, are directly related to dysfunction of the Na/K pump. Exemplary diseases include various cardiac diseases, kidney diseases, especially ischemia-induced kidney failures and kidney-related hypertension, diabetes induced ulcer, Alzheimer diseases and muscle fatigue.

Since active ion transporters involve ion-movements across the cell membrane, the active ion transporters are sensitive to the membrane potential. For example, in the last several decades, significant efforts have been made to electrically control or manipulate the Na/K pumps. However, a practical technique is not currently available that can effectively activate the Na/K pump functions at physiological running conditions. Once the ATP molecules are insufficient, the pump function will be significantly reduced.

Accordingly, what is needed in the art is a system and method for improves the pumping function of active ion transporters.

SUMMARY OF THE INVENTION

In various embodiments, the present invention, referred to as the "$3^{rd}$ generation synchronization modulation technique", provides a system and method for controlling an active ion transporter by applying a $3^{rd}$ generation synchronization modulation electric field ($3^{rd}$ SMEF) which not only synchronizes the active ion transporters, but also provides energy to the active ion transporters so that the active ion transporters can both consume ATP to actively transport ions and synthesize ATP molecules so that the ATP consumption is significantly reduced, and theoretically to zero.

In one embodiment, the present invention provides a method for controlling one or more active ion transporters. The method includes applying an oscillating electric field to an active ion transporter, wherein applying oscillating electric field includes applying a synchronization phase to synchronize the active ion transporters to a physiological turnover rate of the active ion transporters down to individual steps within a running cycle with a net-consumption of adenosine triphosphate (ATP) substantially equal to zero, applying a modulation phase to modulate the synchronized active ion transporters to a predetermined target turnover rate and applying a maintenance phase to maintain the synchronized active ion transporters at the predetermined target turnover rate for a predetermined duration of time.

In the method of the present invention, one ATP molecule is consumed during the running cycle of the one or more active ion transporters and one ATP molecule is synthesized during the running cycle of the active ion transporters, resulting in the net-consumption of ATP of the active ion transporters being substantially equal to zero during the running cycle.

In a particular embodiment, the active ion transporters are Na/K pumps.

In an additional embodiment, the present invention provides a system for controlling an active ion transporter. The system includes an electric field generator to generate and apply an oscillating electric field, wherein the oscillating electric field comprises three serially applied phases. The application of the three serially applied phases of the oscillating electric field include, applying a synchronization phase to synchronize the active ion transporter to a physiological turnover rate of the active ion transporter down to individual steps within a running cycle with a net-consumption of adenosine triphosphate (ATP) substantially equal to zero, applying a modulation phase to modulate the synchronized active ion transporter to a predetermined target turnover rate and applying a maintenance phase to maintain the synchronized active ion transporters at the predetermined target turnover rate for a predetermined duration of time.

In another embodiment, the present invention provides a computer-readable medium storing a set of instructions configured for being executed by at least one processor for performing a method for controlling one or more active ion transporters. The method includes, controlling an electric field generator to apply an oscillating electric field, wherein the oscillating electric field comprises three serially applied phases. The three serially applied phases include, applying a synchronization phase to synchronize the active ion transporter to a physiological turnover rate of the active ion transporter down to individual steps within a running cycle with a net-consumption of adenosine triphosphate (ATP) substantially equal to zero, applying a modulation phase to modulate the synchronized active ion transporter to a predetermined target turnover rate and applying a maintenance phase to maintain the synchronized active ion transporters at the predetermined target turnover rate for a predetermined duration of time.

In a various embodiment, the present invention provides a system and method for synchronizing one or more active ion transporters, such as the Na/K pumps, down to individual steps in the running cycle and for driving the active ion transports in the physiological running conditions to actively transport ions across the cell membrane by consuming one ATP, and simultaneously injecting electric energy to the transporter to synthesize one ATP for each running cycle. As a result, the generated ATP molecules compensates the ATP consumed in actively transporting ions across the cell membrane. The net ATP consumption of the electrically synchronized active ion transporters is significantly reduced, theoretically to zero, and then, gradually modulate or entrain the active ion transporters to a predetermined turnover rate by progressively changing the synchronization frequency of the active ion transporters in a stepwise pattern, wherein the modulation of the active ion transporters consists of two modes: forward modulation to activate the active ion transporters, and backward modulation to deactivate the active ion transporter.

As such, the present invention provides an energy generating synchronization modulation electric field that can utilize electric energy to effectively fuel the activate ion transporters, such as a Na/K pump, and activate or deactivate the turnover rate of the active ion transporter, without ATP consumption.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE INVENTION

Reference will now be made in detail to various examples, examples of which are illustrated in the accompanying drawings. While various examples are discussed herein, it will be understood that they are not intended to be limiting. On the contrary, the presented examples are intended to cover alternatives, modifications, and equivalents, which may be included within the spirit and scope of the various examples as defined by the appended claims. Furthermore, in this Detailed Description of the Invention, numerous specific details are set forth in order to provide a thorough understanding. However, examples may be practiced without one or more of these specific details. In other instances, well known methods, procedures, components, and circuits have not been described in detail as not to unnecessarily obscure aspects of the described examples.

It will be understood that, although the terms first, second, third, without limitation, may be used herein to describe various elements, components, regions, layers, and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of the present invention.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In various embodiments, the present invention provides a system and method for controlling an active ion transporter by applying a specific synchronization modulation electric field which not only synchronizes the active ion transporters down to individual steps throughout the pumping cycle, but also provides electric energy to the active ion transporter so that the active ion transporter can synthesize ATP molecules. The generated ATP compensates the ATP consumed in actively transporting ions, as such the net ATP consumption is significantly reduced, theoretically to zero.

Sodium-potassium (Na/K) pumps are known in biology to be one of many active ion transporters. In the following detailed description, the Na/K pump is used as an example of the process for controlling an active ion transporter. However, the description does not require any specific characteristics of the pump molecules, thus it is within the scope of the present invention to control other active ion transporters by the specially designed energy generating synchronization modulation electric field, as described in more detail below.

Na/K ATPases, or Na/K pump, is a prevalent active transporter in almost all cells. In operation, the pump extrudes 3 Na ions by exchanging 2 K ions to build up Na and K concentration gradients and the potential difference across the cell membrane, thereby providing the critical environment for living cells. The energy stored in the ionic concentration gradient is the source for many member proteins. For example, ion channels utilize the membrane potential to generate and propagate the action potential. Various secondary active transporters use the energy to actively transport sugars, amino acid, etc. From the viewpoint of a physicist, the Na/K pump is a unique energy converter converting ATP hydrolysis energy to the electrochemical potential difference across the cell membrane, so that the membrane proteins can easily use the energy.

Many diseases, and non-physiological conditions, are directly related to dysfunction of the Na/K pump. A short list includes various cardiac diseases, kidney diseases, especially the ischemia-induced kidney failures and kidney-related hypertension, diabetes induced ulcers, Alzheimer diseases and muscle fatigue.

Because Na/K pumps involve ion-transports across the cell membrane, they are sensitive to the membrane potential. In the last few decades significant efforts have been made to electrically control or manipulate the pump functions. Previously, red blood cells have been studied and it was found that a weak oscillating electric field, at a frequency of about 1.0 MHz and 1.0 KHz, can activate the Na- and K-transports, respectively. It was also found that an AC current can either stimulate or inhibit the ATP hydrolysis activity of enzymes, depending on the Na/K ratio. However, there are currently no practice techniques available that can effectively activate the Na/K pump functions while also conserving ATP molecules.

Since discovery of the Na/K pump molecules in the 1950s', Na/K pumps have been considered as progressing through a series of stochastic chemical reactions by random walks among two structural states, E1 and E2, to actively transport Na and K ions across the cell membrane with the pumping cycle reaching a steady-state close to the thermodynamic equilibrium. The two-access-channel model further allocates the protein conformational changes in the "binding pocket" deeply inside the transmembrane domain. Na and K ions are transported from one access-channel to another by the conformational changes in the "binding pocket" including ion-binding, occlusion, de-occlusion, unbinding, etc. Once the pumping cycle is interrupted, without ATP hydrolysis energy, no ion can be actively transported across the cell membrane. Currently, little information is available about the dynamics of this process. As such, it is not clear how the ATP hydrolysis energy released in the cytoplasmic loop fuels the pumping cycle.

To understand the mechanisms involved in the pumping cycle, energy analysis for the Na/K pumps were conducted using skeletal muscle fiber or nerves, as an example. It is known that the Na and K concentration gradients across the cell membrane are equivalent to the Na- and K-potential of 60 mV and −90 mV, respectively. At the membrane resting potential of −90 mV, the energy required to extrude 3 Na ions is 450 meV (=3e (90+60) mV), which is less than the ATP hydrolysis of one ATP of 550 meV (13, 24). It is well known that Na/K pumps run well over a wide range of membrane potentials. At the membrane potential of −123 mV, which is in the range of acceptable membrane running potentials, the energy required to extrude 3 Na ions is increased to 549 meV (=3e (123+60) mV). In other words, in order to run in a wide range of membrane potentials, all the ATP hydrolysis energy must be used to overcome the electrochemical potential difference. As such, there is little or no energy remaining for the required protein conformation change. This energy analysis shows that because of the limited ATP hydrolysis energy, it must be used efficiently. Protein conformational changes inevitably consume energy. In order to run in a wide range of membrane potentials, either there should be no, or little, conformational change in the pumping cycle, or the conformational change must consume little, or zero, ATP.

The PTX-treated pump molecules exhibit the channel functions allowing ions to pass through while the large molecule weight (2690) of PTX makes it impossible to penetrate into the channel to interrupt the "binding pocket". Studies of the reactivity of each amino acid in different transmembrane helices in blockage of the pathway through the PTX-treated pump-channel using the substituted cysteine accessibility method (SCAM) revealed a single unbroken cation pathway that transverses the pump-channel. Most of the cysteines substitutions that affect the channel current are located at either end of the transmembrane domain.

From the viewpoint of physics, an electrostatic force among three or four negative charges in ATP molecules is the origin of ATP hydrolysis energy. Recent studies of energetics of ATP hydrolysis have shown that the energy release from the ATP hydrolysis is not at the time of chemical reaction. Instead, the energy is released at the time of physical separation of phosphate from ADP molecules due to the electrostatic force. The cleaved Pi carrying ATP hydrolysis energy moving away from ADP provides foundation such that the ATP energy can drive 3 Na ions out of the cell. In other words, 3 Na ions carry the ATP hydrolysis energy of 550 meV as the mechanic energy moving out of the cell.

In terms of the driving force of K ions, when the membrane potential is less hyperpolarized, the energy required for Na-extrusion is reduced and the energy required for K-pumping in is increased. The energy remaining on 3 Na ions when reaching the extracellular solution is always larger than the energy required for 2 K ions pumping in. For example, at the membrane potential of −70 mV, the energy required for Na-extrusion is only 390 (=3×(70+60)) meV, while pumping-in 2 K ions requires 40 (=2×(90−70)) meV. The energy of 160 meV remaining on 3 Na ions, when transferred to the K-transport, is more than enough to drive-in 2 K ions freely and mechanically moving across the cell membrane.

Based on these results, a dynamic model of the has been developed Na/K pump. A first hypothesis is that Na and K ions freely and mechanically move across the cell membrane without conformational change in the transmembrane domain. Secondly, Na and K ions carry energy when mechanically moving across the cell membrane to overcome the potential differences. Ions movements across the cell membrane are deterministic instead of through random walk. In other words, the Na/K pump is considered to be a microscopic machine. Two ion-movements across the cell membrane function like two power-strokes in the pumping cycle.

Na/K pumps have many pumping modes. In addition to the normal mode consuming ATP to develop concentration gradients, and some non-canonical modes, such as K—K exchange mode, Rb—Rb exchange mode and Na/Na exchange mode Na potential energy stored in the Na concentration gradient is transformed to the mechanic energy of the down-stream Na ions to re-phosphorylate ADP to synthesize ATP. Similarly, for ATP synthesizers, such as bacteriorhodopsin and F0F1-ATPases, proton potential energy is also transformed into the mechanic energy of the downstream protons to rotate the F0 domain in F0F1 ATPase to synthesize ATP.

Accordingly, the present invention combines the intrinsic mechanisms involved in the normal pumping mode and in the non-canonical model into a dual energy-transform function. In operation, the pumps are run at normal mode to extrude 3 Na and to pump in 2 K ions by consuming one ATP molecule, while simultaneously injecting electrical energy (same category as the chemical potential energy) to the pumps. As a result, the pump is capable of consuming ATP to transport ions, while also using the injected energy, instead of the Na potential energy, to synthesize ATP. As a result, the net ATP-consumption will be significantly reduced, theoretically to zero.

The question becomes how to inject enough energy (based on energy conservation law, at least 550 meV, the ATP hydrolysis energy) to each pump molecule for one pumping cycle so that the pump can synthesize one ATP in the cycle. Based on physics, when an electric field is applied along the ion movements, the electric field will accelerate the moving ions, or the ions will absorb electrical energy. In the proposed dynamic model, Na and K ions freely move across the cell membrane, thereby providing two time-windows to inject electric energy to the pumps.

In the present invention, the $3^{rd}$ generation synchronization modulation technique, provides a method to electrically fuel an active ion transporter and control the turnover rate of the active ion transporter, such as a Na/K pump, to a pre-determined value with less or zero consumption of ATP.

There are three steps in the technique. Pump molecules have individual structures running independently at a random pumping pace. It is impossible for one electric field to handle all the pump molecules. Therefore, the first step is to force the physiologically random paced pump molecules to run at the same pumping pace, down to individual steps, throughout the pumping cycle.

By employing a first-generation synchronization modulation technique of the present invention, the Na/K pump molecules can be synchronized up to two ion-transports and activate the pump functions in the presence of ATP molecules. By employing a second-generation synchronization modulation technique, the Na/K pumps can be synchronized, at running conditions, down to individual steps throughout the pumping cycle. However, both the first-generation synchronization technique and the second-generation synchronization modulation technique require the presence of ATP molecules.

In a second step, electric energy is injected to the pump molecules, twice per cycle, alternatively and accurately through the ion-movements, so that the energy accumulated in the pump molecule is sufficient to synthesize one ATP molecule.

In a third step, modulation of the pumping rate is performed to modulate, or entrain, the pump molecules to run at a specific pre-determined turnover rate. Once the pump molecules are well synchronized, the oscillating frequency of the electric field can be gradually increased or decreased with a stepwise pattern to modulate the pumping rate to a pre-determined value.

As such, the third-generation synchronization modulation electric field (SMEF) technique of the present invention consists of three phases. Phase 1 is to synchronize the Na/K pumps down to the individual steps throughout the pumping cycle in actively transporting Na and K ions without ATP consumption. Phase 2 is to modulate the pumping rate of the synchronized pump molecules to a pre-determined target value. Phase 3 is to maintain the pumping rate at the target value for a certain period, based upon the clinical requirement.

Figure 1:
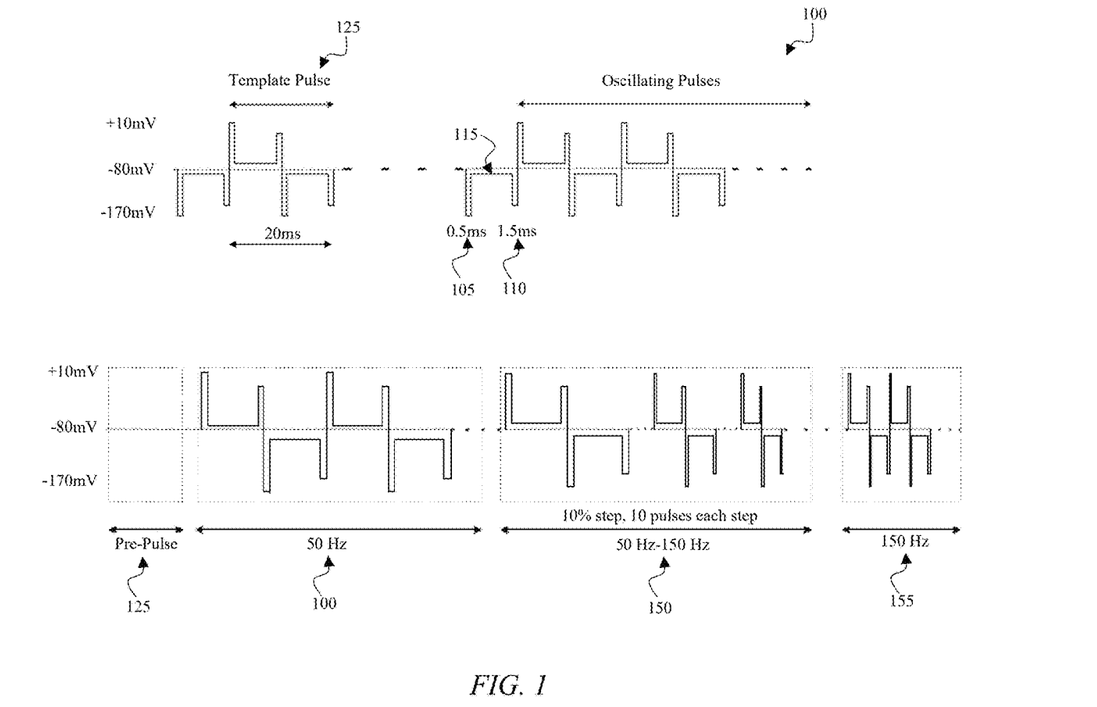
FIG. 1 illustrates the waveform of the present invention, the $3^{rd}$ generation synchronization modulation electric field.

FIG. 1 illustrates the waveform of the present invention, referred to herein as the $3^{rd}$ generation synchronization modulation electric field. In the synchronization phase 100, the electric field is a pulsed, symmetric, oscillating electric field consisting of two overshoot electric pulses in each half-cycle. First, is the activation overshoot electric pulse 105 with a duration of about 0.5 ms, or less, and a magnitude greater than about 90 mV followed by a plateau 115 of about 20 mV. Next, is the energy-trap overshoot electric pulse 110 having a duration of about 1.5 ms, or less, and a magnitude of about 70 mV.

It is noted that the magnitude of the electric field illustrated in FIG. 1 is applicable to the voltage-clamp experiments, or the potential difference across the cell membrane. For clinical applications, the applied field-strength should be adjusted to apply the proper electric field for the situation of the tissues and organs. The oscillating frequency is comparable to the natural turnover rate of the transporter used to synchronize the active ion transporters, or the Na/K pumps.

Also shown in FIG. 1 is a pre-pulse 125 that may be applied before the application of the oscillating electric field. The pre-pulse has the same waveform as the oscillating pulses. The pre-pulse 125 is used when the synchronized pump currents need to be identified. The currents generated by the pre-pulse 125 serve as the template to be subtracted from the currents generated by the individual oscillating pulses, with the resulting difference being the synchronized pump currents.

As such, the three phases of the oscillating electric field, in accordance with embodiments of the present invention, are illustrated in FIG. 1, wherein the pre-pulse 125 and the synchronization phase 100 are shown, as previously described, in addition to the modulation phase 150, where the oscillating frequency is gradually increased from about 50 Hz to about 150 Hz in a stepwise pattern, and the maintenance phase 155, where the field oscillating frequency remains at the target frequency.

In the modulation phase 150, the synchronization frequency or the frequency of the oscillating electric field will be gradually changed, going up or going down, to progressively modulate or entrain (accelerate or decelerate) the pump molecules to a pre-determined pumping rate. The waveform remains the same as that in the synchronization phase, and the oscillating frequency is gradually increased or decreased in a stepwise pattern (3% to 10% of the frequency change for 10 to 20 oscillating pulses) to a target frequency. By carefully maintaining the pump synchronization and gradually increasing or decreasing the synchronization frequency, the pump molecules can be entrained to higher and higher, or lower and lower, pumping rate, respectively, to reach a pre-determined value.

For the maintenance phase of the $3^{rd}$ SMEF, the frequency of the oscillating electric field is kept at the target frequency for a certain period of time, as determined by the specific requirement of the application. The waveform of the oscillating electric field remains unchanged.

For future applications, the 3rd-SMEF has been specifically designed to avoid side effects on the cell membrane. For example, to avoid changing the integrity of the cell membrane the field-induced membrane potentials are in physiological range, much lower than the thresholds of membrane electroporation and protein denature. The short duration of the overshoot pulses (a few hundred microseconds) is not long enough to open the voltage-gated ion channels, including the Na-channels having the fastest electric response, or effect other membrane proteins. The oscillating waveform of the 3rd-SMEF was specifically designed for Na/K pumps, transporting cations in the opposite direction, and the 50 Hz frequency is comparable to the turnover rate of Na/K pumps, which is far away from other pumps, such as Ca2+ pumps of 500 Hz.

FIG. 2A-FIG. 2H illustrate the Na/K pump currents generated by various stimulation pulses. The experiments were performed on skeletal muscle fiber using a whole-cell path-clamp technique in the presence of extremely low ATP by exchanging the internal solution with the washing-out solution without ATP, ADP and inorganic phosphate but with 200 nM AMA, the ATP synthesizer inhibitor for at least five times, whereby the ATP concentration cannot support the functions of the Na/K pumps.

Figure 2A:
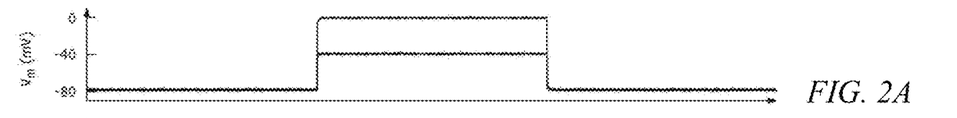
FIG. 2A illustrates exemplary traditional stimulation pulses of 100Ms, 40 mV and 80 mV applied to Na/K pumps.
Figure 2B:
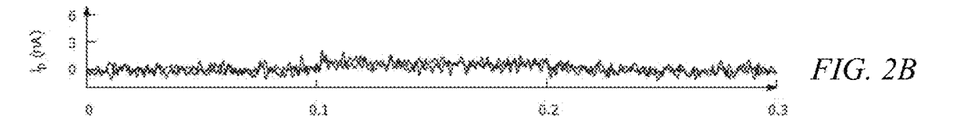
FIG. 2B illustrates the Na/K pump currents resulting from the stimulation pulses of FIG. 2A.

FIG. 2A illustrates traditional stimulation pulses of 100 ms, 40 mV and 80 mV. The generated ouabain- or digoxin-sensitive pump current is zero, as shown in FIG. 2B. This confirms that the cytoplasmic ATP is extremely low and cannot support the Na/K pumps.

Figure 2C:
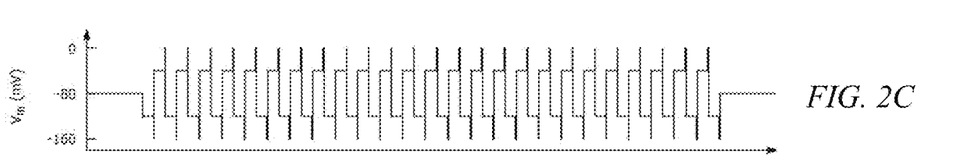
FIG. 2C illustrates various exemplary modified $3^{rd}$-SEF stimulation pulses applied to Na/K pumps.
Figure 2D:
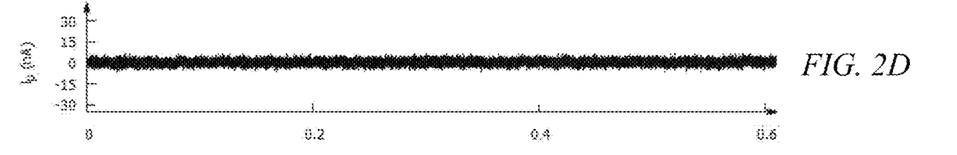
FIG. 2D illustrates that no Na/K pump currents are generated as a result of the stimulation pulses of FIG. 2C.

Next, various modified 3rd-SEF (for example, removal of the first overshoot pulse, or the activation overshoot electric pulse, named 2nd-SEF, FIG. 2C, or the second overshoot, not shown). No pump currents could be generated, as shown in FIG. 2D.

Figure 2E:
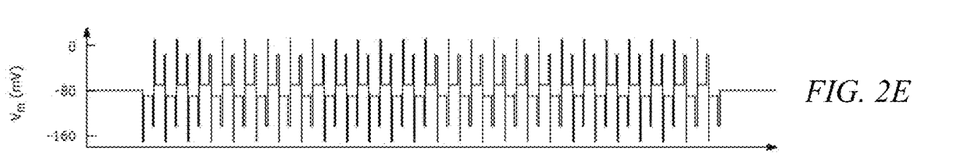
FIG. 2E illustrates exemplary stimulation pulses based upon the $3^{rd}$ generation synchronization modulation electric field applied to Na/K pumps.
Figure 2F:
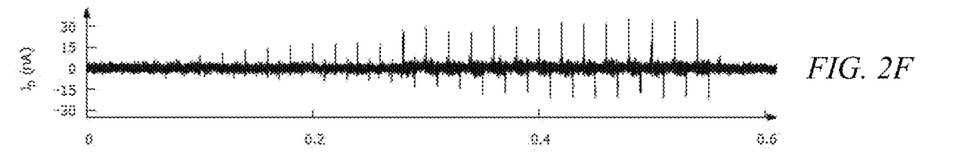
FIG. 2F illustrates the Na/K pump currents resulting from the stimulation pulses of FIG. 2E.
Figure 2G:
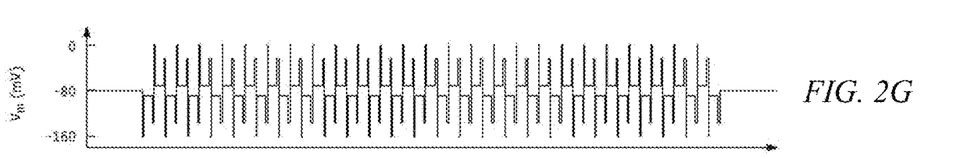
FIG. 2G illustrates exemplary stimulation pulses based upon the $3^{rd}$ generation synchronization modulation electric field applied to Na/K pumps.
Figure 2H:
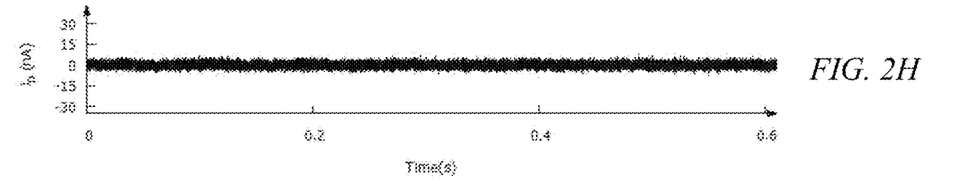
FIG. 2H illustrates that the Na/K pump currents resulting from the stimulation pulses of FIG. 2G, and in the presence of ouabain, are fully eliminated.

Finally, the first phase of the $3^{rd}$ generation synchronization modulation electric field, or the synchronization electric field (3rd-SEF), shown in FIG. 2E, was applied to the cell membrane, which generates separated, transient outward and inward currents responding to the start of the activation overshoot electric pulse in the positive and negative half-cycle, respectively, as shown in FIG. 2F. In the presence of ouabain, the transient currents were fully eliminated in response to the start of the activation overshoot electric pulse in the positive and negative half-cycle of FIG. 2G, as shown in FIG. 2H. This confirms that the separated transient currents are the Na/K pump currents, or under the $3^{rd}$ SMEF, Na/K pumps can each extrude 3 Na ions and pump in 2 K ions, regardless of the extremely low ATP concentration, or the 3rd-SEF can maintain the physiological functions of the Na/K pump without ATP consumption.

Figure 3:
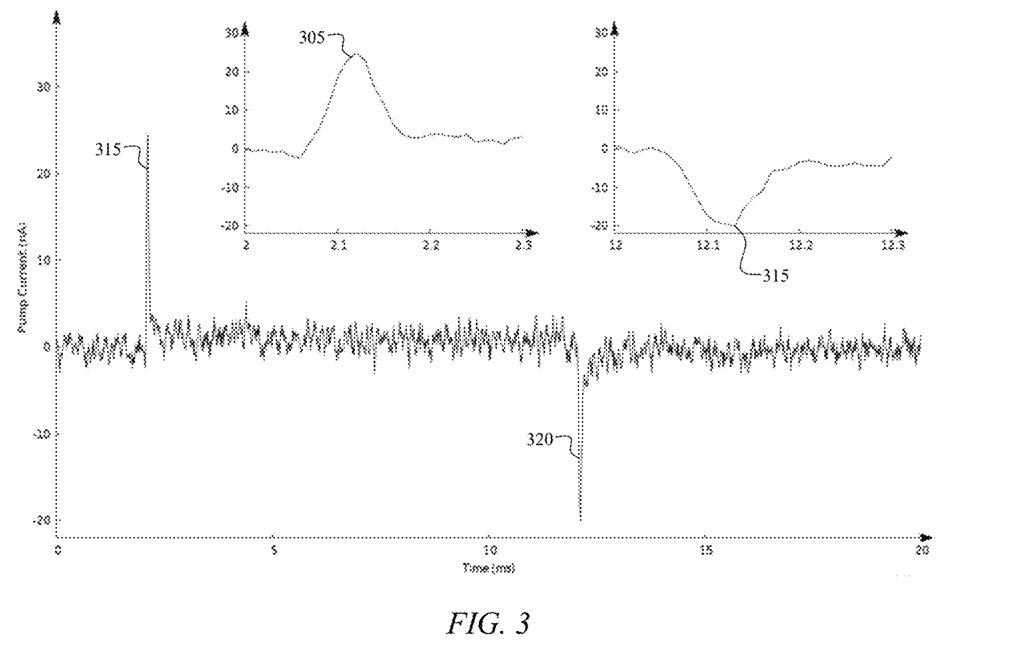
FIG. 3 illustrates a pair of the outward Na and inward K pump currents from the synchronized Na/K pumps, in accordance with an embodiment of the present invention.

One pair of the transient pump currents responding to the positive and negative half-pulses are shown in FIG. 3. The magnitude of the pulses is 25 nA 305 and −19 nA 310, respectively, with a ratio of 3:2, the stoichiometric ratio of Na/K pumps, which further confirms the Na/K pump currents. Interestingly, both the positive 315 and negative transient pump currents 320 have an extremely short duration of 100 ms, much shorter than any ion-channel currents, including the voltage-gated Na channels (1 ms), which have the fastest electrical response. Duration of the pump currents is similar to the membrane capacitance currents.

Figure 4:
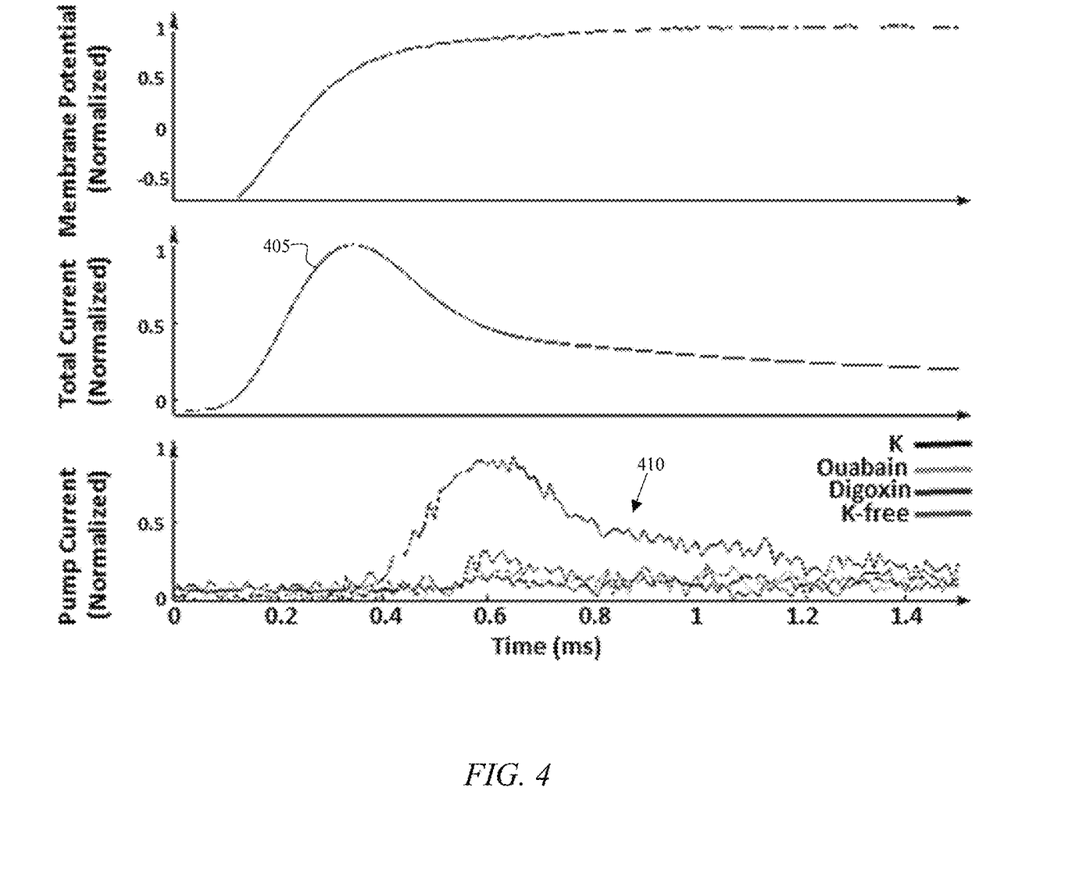
FIG. 4 compares duration of the transient Na/K pump currents and the total transmembrane currents (mainly the capacitance currents) at low gain of the voltage-clamp, in accordance with the present invention.

To confirm that pump currents and the membrane capacitance currents have a similar duration, the gain of the voltage-clamp was purposely increased or decreased to shorten or expand the duration of transmembrane (primarily the capacitance) currents. Regardless of the changes in gain, it was shown that they always have a similar duration. As shown in FIG. 4, gain reduction expanded the transmembrane currents to about 400 μs 405, while the pump currents also increased to about 400 μs 410.

Duration of the pump currents, which are shown to be faster than any ion-channel currents and similar to the membrane capacitance currents, confirms that Na and K ions carry energy freely and mechanically move across the cell membrane against the potential differences.

Figure 5:
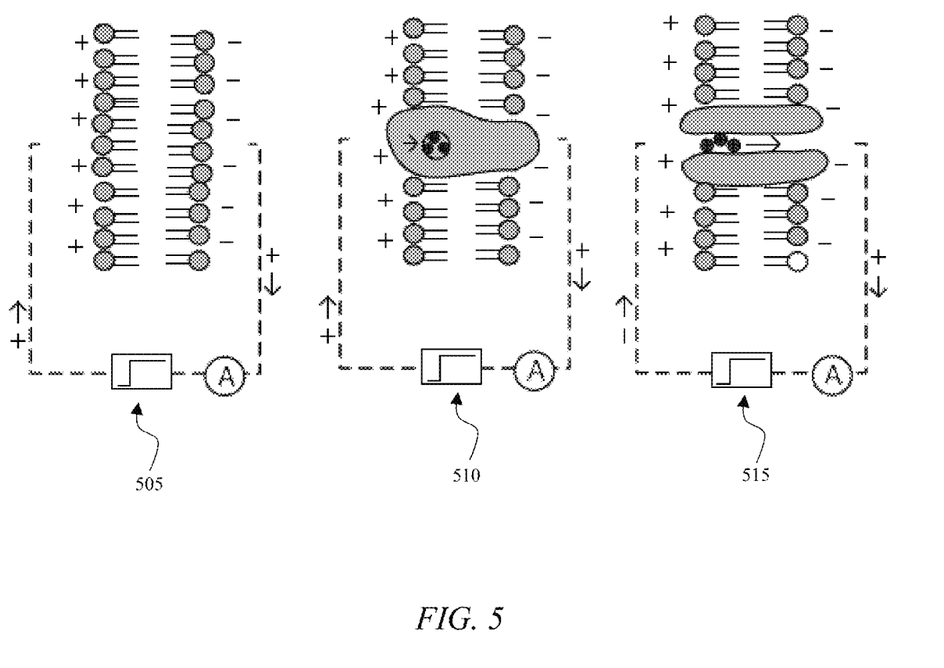
FIG. 5 illustrates the pathway for the capacitance currents and transmembrane currents (carrier-mediated pump currents or through a channel-like structure), in accordance with embodiments of the present invention.

FIG. 5 provide illustrations showing the difference between the membrane capacitance currents 505, carrier-mediated ion-transporter 510 and the Na/K pumps 515. As shown in 505, capacitance currents represent ion-drifting in solution to charge the membrane capacitance without any biological event involved. Illustration 510 represents the protein conformational changes which carry ions moving across the cell membrane. Because conformational change is involved, it will become the rate-limiting step, inevitably slowing down the time-course of the pump current. In illustration 515, Na and K ions freely and mechanically move across the cell membrane through a channel-like structure, which can be observed by the similar duration of the transient pump currents and the capacitance currents, as previously shown in FIG. 4, indicating that the time for the ion-movements across the cell membrane is much shorter than the time in charging the membrane capacitance. The Na/K pump is also different from the ion-channels, where a large number of ions diffuse across the cell membrane, driven by the concentration gradient and/or electric field while for the pumps, only 2 or 3 ions carry energy to move across the cell membrane, freely and mechanically against the potential difference. As a result, the duration of the pump current is much shorter than the ion-channel current and is also similar to the membrane capacitance current.

These results confirm that Na and K ions freely move across the cell membrane without conformational change in the transmembrane domain, as shown in illustration 515 of FIG. 5, and that the ions carry energy to mechanically move across the cell membrane against the potential difference.

Figure 6:
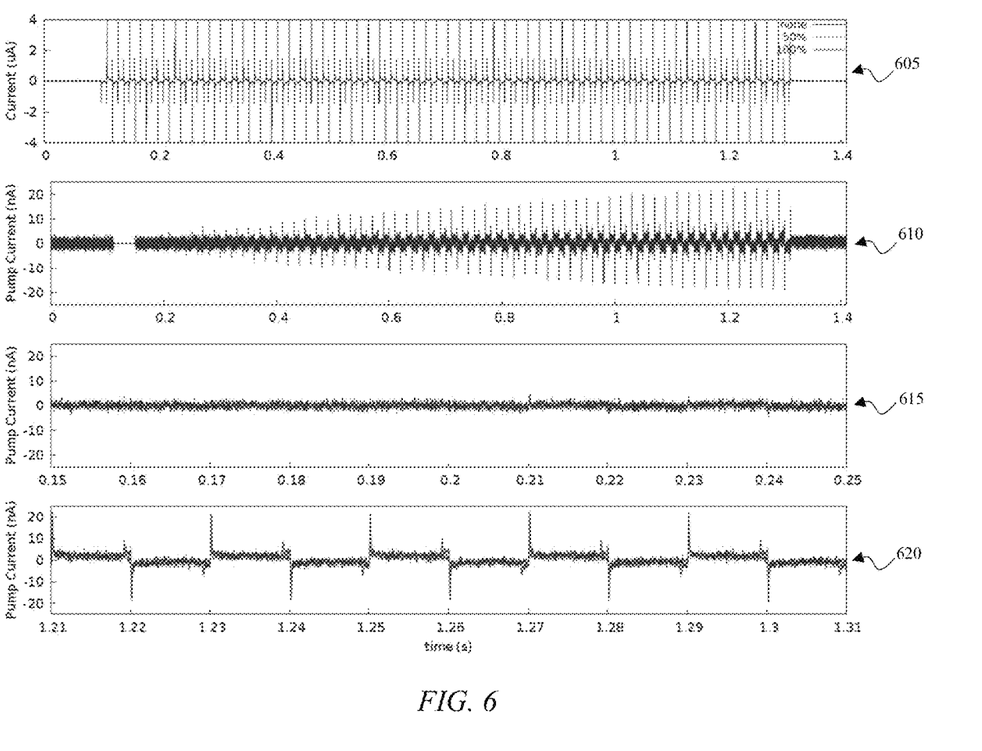
FIG. 6 illustrates the first phase, or synchronization phase, of the $3^{rd}$ SMEF induced Na/K pump currents, in accordance with embodiments of the present invention.

FIG. 6 shows another group of experiments to study the effects of the first phase of the present invention, the 3rd SEF on the Na/K pumps. In this experiment, the stimulation pulses consist of 60 pulses. Illustration 605 of FIG. 6 shows the elicited total transmembrane currents (in μA).

After subtracting the currents generated by the pre-pulse, the synchronized Na/K pump currents are shown in illustration 610 if FIG. 6 (in nA). For the first a few oscillating pulses, there are no pump currents at all because the pump molecules remained randomly paced. As more and more of the Na/K pumps are synchronized, the separated transient outward Na and inward K currents responding to the start of the activation overshoots for the positive and negative half-pulses, respectively, gradually increased, until saturation. Magnitude of the transient pump currents is much (tens of times) larger than the net outward pump currents from the random paced pumps. The outward Na pump currents are a little larger than the inward K currents, reflecting the stoichiometric ratio of 3:2. Illustration 615 and 620 show the transient pump currents in response to the first and last five oscillating pulses, respectively.

Figure 7A:
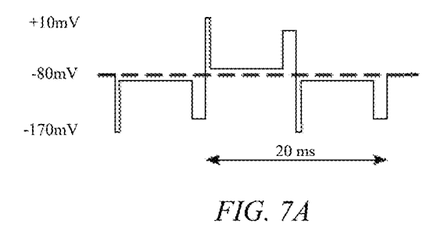
FIG. 7A illustrates the waveform of the synchronization phase, or first phase, of the $3^{rd}$ generation synchronization modulation electric field, in accordance with embodiments of the present invention.
Figure 7B:
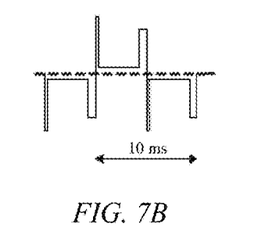
FIG. 7B illustrates the waveform of the modulation phase, or second phase, of the $3^{rd}$ synchronization modulation electric field, in accordance with embodiments of the present invention.
Figure 7C:
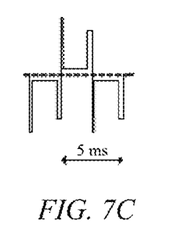
FIG. 7C illustrates the waveform of the maintenance phase, or third phase, of the $3^{rd}$ synchronization modulation electric field, in accordance with embodiments of the present invention.

FIG. 7A-FIG. 7C show exemplary waveforms of the three phases of the 3rd generation synchronization modulation electric field of the present invention. FIG. 7A illustrates the synchronization phase to synchronize the random paced Na/K pump running at the same pace down to individual steps throughout the pumping cycle. FIG. 7B illustrates the modulation phase, wherein after about 30 to 50 oscillating pulses, the pump molecules will be well synchronized so that the outward Na and inward K pump currents are restricted to the start of the activation overshoot electric pulses in the positive and negative half-pulses, respectively. Then, the oscillating frequency will be gradually changed (increased or decreased) using a stepwise pattern (3% to 10%) of the frequency for every five to ten oscillating pulses to a pre-determined value of 200 Hz. FIG. 7C illustrates the maintenance phase to keep the pumping rate at the target value for a certain period of time.

Figure 8:
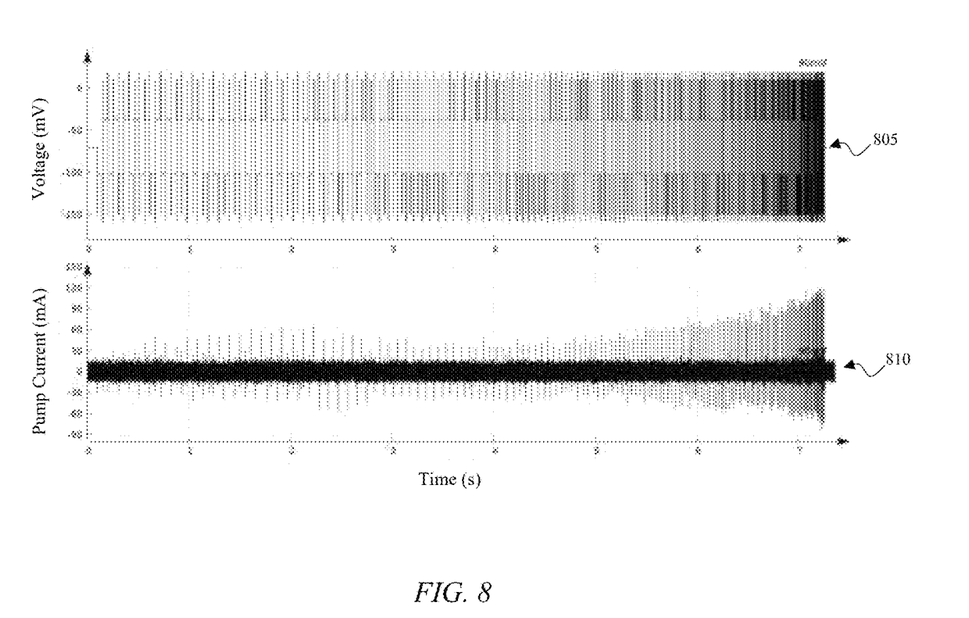
FIG. 8 illustrates the synchronized and activated Na/K pump currents in the presence of extremely low ATP concentration generated by the $3^{rd}$ forward SMEF, in accordance with the present invention.

Illustration 805 of FIG. 8 shows the $3^{rd}$ SMEF with the target synchronization frequency of 200 Hz. Illustration 810 of FIG. 8 shows the synchronized and modulated pump currents, after subtraction of the template currents from the pre-pulses in the presence of extremely low ATP concentration. It should be pointed out that as the synchronization frequency gradually increased, not only the magnitude of pump currents but also the current density (number of transient pump currents per second) is significantly increased. In other words, functions of the pump molecules or the number of extruded Na ions and pumped-in K ions are dramatically increased.

The effects of the method of the present invention on the maintenance of the membrane potential of skeletal muscle fibers were analyzed. The function of Na/K pumps is to maintain ionic concentration gradients across cell membrane which can be expressed as the Na and K equilibrium potentials. The membrane potential is a weighted summation of the positive Na-equilibrium potential and negative K-equilibrium potential. Because the membrane leakage for K ions is much larger than that for Na ions, the membrane resting potential is mainly determined by the K-equilibrium potential. Due to the leakage of cell membranes, the ionic concentration gradients are inevitably gradually reduced, or the membrane potential is depolarized. At physiological conditions, functions of the Na/K pumps compensate the membrane leakage to maintain the membrane resting potential. However, once the pumps somehow stop running, the membrane potential will be slowly, but continuously, depolarized. On the other hand, activation of the Na/K pumps which increases the K concentration gradient, or the value of K-equilibrium potential should hyperpolarize the membrane potential.

Figure 9A:
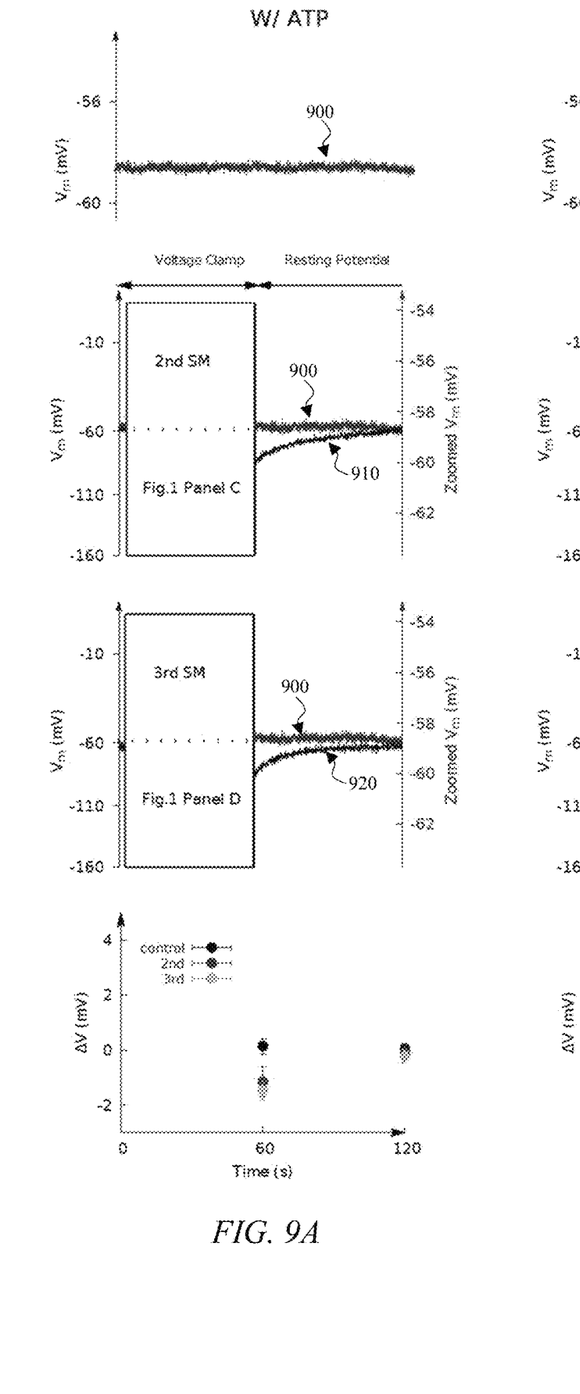
FIG. 9A illustrates membrane potential changes as a function of time with and without application of different electric fields in the presence of physiological ATP concentration, in accordance with embodiments of the present invention.
Figure 9B:
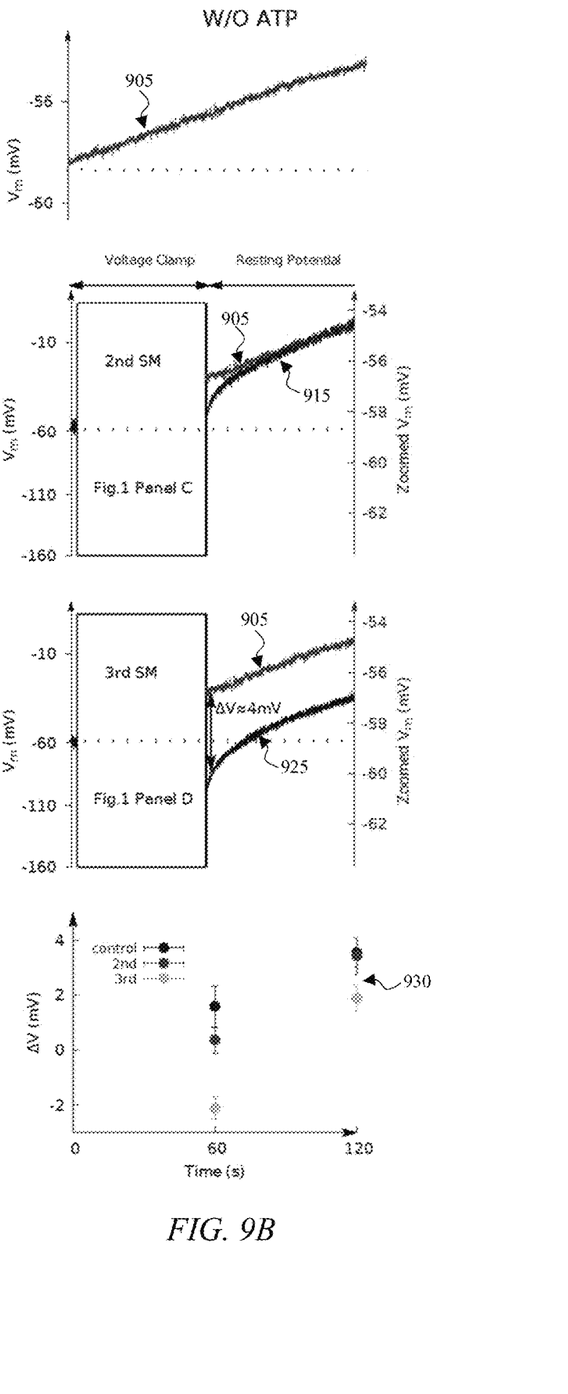
FIG. 9B illustrates membrane potential changes as a function of time with and without application of different the electric fields in the presence of extremely low ATP, in accordance with embodiments of the present invention.

FIG. 9A and FIG. 9B illustrate the membrane potential changes in the normal physiological or in the presence of extremely low ATP molecules, respectively, with or without the application of the $3^{rd}$ SMEF, the present invention. Traces 900 and 905 represent the control without the electric field application of the present invention. As shown, in the presence of physiological ATP concentration (900), Na/K pumps run well so that the membrane potential remains at a constant value of about −58.5 mV. However, in the presence of extremely low ATP molecules (905), the membrane potential gradually depolarized to −56.5 mV at 60 s and further to −54.5 mV at 120 s.

Next, the modified $3^{rd}$ SMEF (removing the activation overshoot electric pulse or the energy-trap overshoot electric pulse) was applied to the cell membrane through the voltage-clamp in clamping mode for 60 s (rectangular box). The fiber was held at the membrane resting potential right before switching to the clamp mode. Once the field application is over, the voltage-clamp was changed to the monitor model to measure the membrane potential change. The field-induced membrane potential change is shown as traces 910 and 915 superimposed with traces 900, and 905 in FIGS. 9A, and 9B, respectively. In the presence of normal ATP concentration, the field application depolarized the membrane potential for 1.5 mV (910). Once the field application was removed, membrane potential was depolarized merging to the membrane resting potential (900). In the presence of extremely low ATP, there was no membrane hyperpolarization, after removal of the electric field, again, the membrane potential (915) quickly merged to the control (905) without the field application.

Next, the synchronization oscillating electric field of the present invention, the $3^{rd}$ SMEF, with the magnitude of activation overshoot of 100 mV was applied to the cell membrane through a voltage-clamp for 60 s (rectangular box). The results are shown as traces 920 and 925 superimposed with the traces 900 and 905 as the control. In the presence of ATP molecules, the oscillating electric field hyperpolarized the membrane potential for about 1.5 mV (920). Once the electric field is over, the membrane potential gradually returned to the resting membrane potential. Interestingly, in the presence of extremely low ATP, the electrical field also hyperpolarized the membrane potential for about the same value (925). Then, the membrane potential was quickly depolarized until parallel to 905 but maintaining a 2.5 mV difference 930. Clearly, the $3^{rd}$ SMEF of the present invention protects the membrane potential depolarization, or the field-induced activation of the Na/K pumps can effectively maintain the membrane potential at extremely low concentrations of ATP.

In a particular embodiment, the present invention, the $3^{rd}$ generation modulation electric field was also used to maintain the transepithelial potential difference (TEPD) for the ischemia-injured kidney. In kidneys, the Na/K pump is highly expressed on the basolateral surface of tubular epithelial cells. The ischemia induced dysfunction of the Na/K pump depolarizes the membrane potential and therefore reduces the transepithelial potential difference. The experiments were performed on the isolated kidney from rat.

Figure 10:
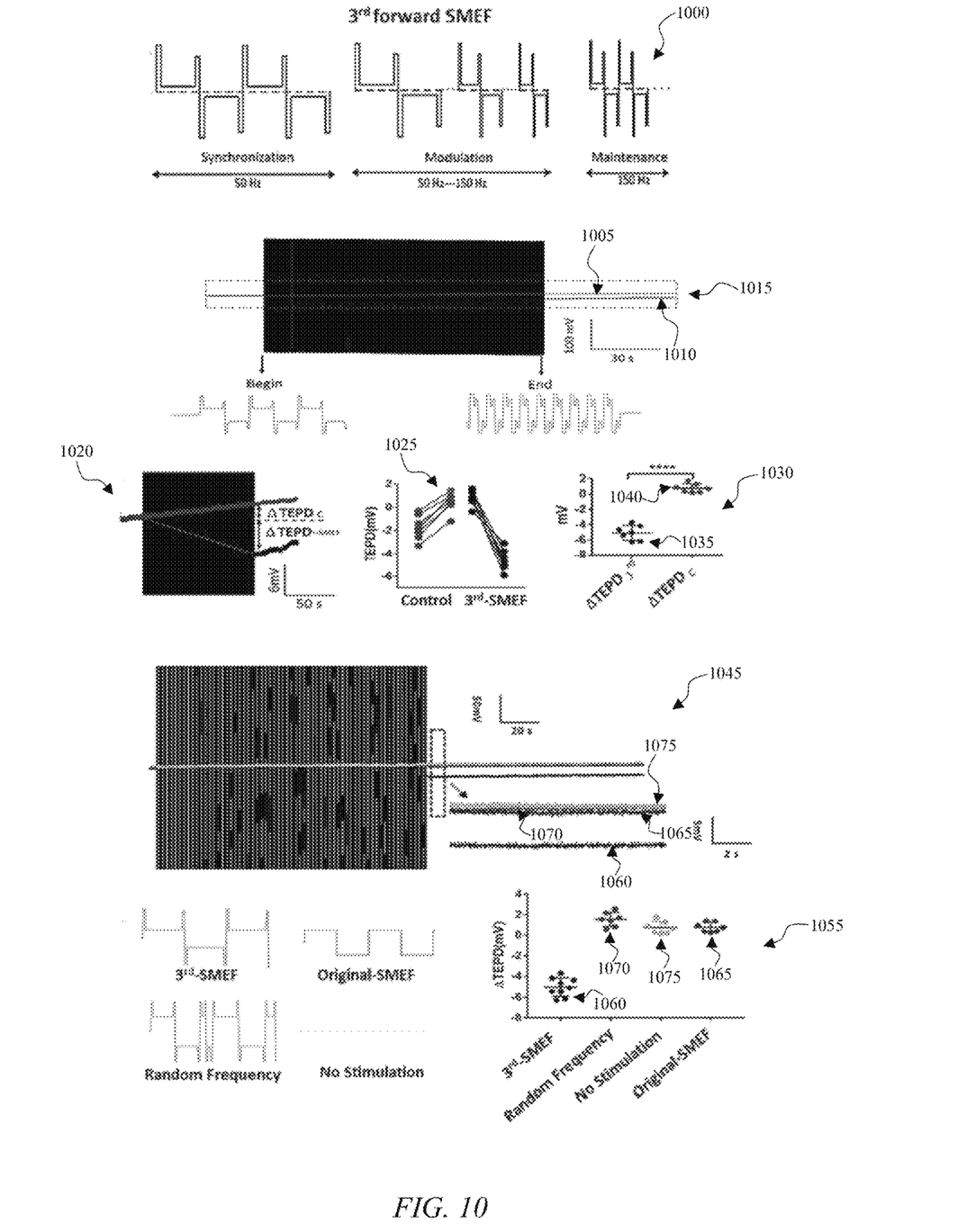
FIG. 10 illustrates measurements of the transepithelial potential difference (TEPD) from proximal tubule of kidney, waveform of the oscillating electric field in three phases, in accordance with embodiments of the present invention.

FIG. 10 shows the effects of the $3^{rd}$ forward SMEF on TEPD measured from the isolated kidney from rat, where the pedicle blood vessel was clamped to avoid bleeding. The experiments were conducted within one hour after the kidney was isolated from the rat, where the TEPD was measured by the micro-electrode technique. Illustration 1000 shows the waveform of three phases for the 3rd forward SMEF with the target frequency of 150 Hz. Due to clamping the pedicle blood vessel, ATP concentration in kidney is decreased resulting dysfunction of Na/K pumps.

As shown in illustration 1015, as a result, TEPD was gradually decreased from −1 mV to 1 mV in about 120 s as a control 1005. In contrast, application of the 3rd forward SMEF increased the TEPD to −5 mV 1010. The detailed changes are shown in illustration 1020. Seven experiments were performed, as shown in illustration 1025, and the statistic results for the TEPD changes are shown in illustration 1030 for the control 1035 and $3^{rd}$ forward SMEF 1040. The 3rd forward SMEF 1040 not only maintains but also increases the TEPD to −5 mV, which is 6 mV difference from the control 1035.

Illustration 1045 compares the rescue effects from different electric fields 1050 on the reduced TEPD, including the 3rd forward SMEF (1060), 1st forward SMEF (1065), random frequency (1070), and no stimulation (1075). TEPD changes measured in dashed-line box is enlarged and shown as the insert. As shown in the insert of illustration 1045, only the 3rd forward SMEF (1060) increased the TEPD. Illustration 1055 is the statistic result of ΔTEPD from seven experiments. The long bars are the mean values. As shown in illustration 1055, only the 3rd forward SMEF increased the TEPD to about −5 mV. The results proved that the 3rd forward SMEF is capable of maintaining, or even increasing the TEPD, to rescue the epithelial cells from the ischemia injury.

All experimental results were conducted in the presence of extremely low ATP concentrations that cannot support the Na/K pump functions. The Na/K pump currents showing extrusion of Na ions and pumping in of K ions, the maintenance of the membrane potential, and the transepithelial potential difference all require ATP molecules to fuel the Na/K pumps. The results show that under the present invention, the $3^{rd}$ generation synchronization modulation electric field, ATP molecules are not consumed but only recycled in the pumping cycle. In other words, the $3^{rd}$ SMEF utilizes the electric energy to substitute the ATP hydrolysis energy to fuel and activate the pumping cycle without ATP consumption.

It is necessary to point out the studies shown here are different from previous studies of the non-canonical Na/Na exchange modes on the Na/K pumps even though the zero net-ATP consumption is the same. For the Na/Na exchange mode, the same number of Na ions are exchanged among two sides of the cell membrane, or no work is done, while here, without consumption of ATP molecules, the ionic concentration gradient is increased, and the membrane potential is hyperpolarized. In other words, it is the electric energy substituting the ATP hydrolysis energy to do work in development of the ionic concentration gradients and the membrane potential.

In summary, the energy generating synchronization modulation electric field of the present invention, referred to herein as "the $3^{rd}$ generation synchronization modulation electric field", is a practical technique that can effectively activate the function of Na/K pumps to develop the ionic concentration gradient and the membrane potential with less or even zero ATP-consumption. Moreover, the synchronization techniques were developed based on the dynamic model of the pump molecules. The successful synchronization modulation of the pumping rate and the substitution of ATP energy to fuel the pumping in the buildup of the ionic concentration gradients and the membrane potential support the dynamic model of the Na/K pumps as a microscopic machine.

As such, in various embodiments, the present invention provides a system and method for controlling an active ion transporter by applying an energy generating synchronization modulation electric field which not only synchronizes the active ion transporter, but also synthesizes ATP to provide enough energy to the pump molecules of the active ion transporter.

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C #, C++, Visual Basic or the like and conventional procedural programming languages, such as the "C" programming language or similar programming languages.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

What is claimed is:

1. A method for controlling active ion transporters, the method comprising:
applying an oscillating electric field to one or more active ion transporters, wherein the oscillating electric field comprises three serially applied phases and wherein applying the oscillating electric field comprises;
applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter sis in a negative half-cycle and the ion-extrusion half-cycle of the active ion transporters is in a positive half-cycle of the oscillating electric field and wherein applying the synchronization phase further comprises:
applying an activation overshoot electric pulse at a start of the negative half-cycle and at a start of the positive half-cycle of the oscillating electric field;
applying an energy-trap overshoot electric pulse at an end of the negative half-cycle and at an end of the positive half-cycle of the oscillating electric field; and
applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;
applying a modulation phase to modulate the synchronized active ion transporters to a predetermined target turnover rate; and
applying a maintenance phase to maintain the synchronized active ion transporters at the predetermined target turnover rate for a predetermined duration of time.

2. The method of claim 1, wherein one ATP molecule is consumed during the running cycle of the one or more active ion transporters and one ATP molecule is synthesized during the running cycle of the active ion transporters, resulting in the net-consumption of ATP of the active ion transporters being substantially equal to zero during the running cycle.

3. The method of claim 1, wherein the synchronization phase further restricts an outward transporter current at the start of the activation overshoot electric pulse in the positive half-cycle and restricts an inward transporter current at the start of the activation overshoot electric pulse in the negative half-cycle of the oscillating electric field.

4. The method of claim 1, wherein a membrane potential of the active ion transporters is hyperpolarized in response to the activation overshoot electric pulse and the energy-trap overshoot electric pulse during the negative half-cycle of the oscillating electric field, and wherein the membrane potential of the active ion transporters is depolarized in response to the activation overshoot electric pulse and the energy-trap overshoot electric pulse during the positive half-cycle of the oscillating electric field.

5. The method of claim 1, wherein a magnitude of the activation overshoot electric pulse is sufficient to allow the active ion transporters to operate within a physiological range of a membrane potentials of the active ion transporters and wherein a magnitude of the energy-trap overshoot electric pulse is sufficient to allow the active ion transporters to operate within a physiological range of the membrane potentials of the active ion transporters.

6. The method of claim 1, wherein a duration of the activation overshoot electric pulse is about 1 ms or less and a magnitude of the activation overshoot electric pulse is at least about 90 mV.

7. The method of claim 1, wherein a duration of the energy-trap overshoot electric pulse is about 1.5 ms or less and a magnitude of the energy-trap overshoot electric pulse is about 70 mV.

8. The method of claim 1, wherein the electric field plateau is about 20 mV between the activation overshoot electric pulse and the energy-trap overshoot electric pulse.

9. The method of claim 1, wherein a frequency of the oscillating electric field during the synchronization phase is substantially equal to the physiological turnover rate of the active ion transporters.

10. The method of claim 1, wherein applying the modulation phase further comprises:
applying an oscillating electric field wherein a waveform of the oscillating electric field is identical to the oscillating electric field in the synchronization phase, and the magnitude of the activation overshoot electric pulse and the energy-trap overshoot electric pulse is the same as the magnitude of the activation overshoot electric pulse and the energy-trap overshoot electric pulse in the synchronization phase, respectively, and the duration of the activation overshoot electric pulse and the energy-trap overshoot electric pulse is the same as the duration of the activation overshoot electric pulse and the energy-trap overshoot electric pulse in the synchronization phase, respectively.

11. The method of claim 1, wherein applying the modulation phase further comprises applying a forward modulation wherein a frequency of the oscillating electric field is gradually increased to accelerate a turnover rate of the active ion transporters to the predetermined target turnover rate and applying a backward modulation wherein the frequency of the oscillating electric field is gradually decreased to decelerate the active ion transporters to the predetermined target turnover rate.

12. The method of claim 11, wherein gradually increasing and decreasing the frequency of the oscillating electric field is performed in a stepwise pattern, where the frequency is changed from about 3% to about 10% and repeated for approximately 5 to 10 oscillating pulses at the frequency.

13. The method of claim 1, wherein applying the maintenance phase comprises applying a waveform and a frequency of the oscillating electric field that is equivalent to a waveform and a frequency of the oscillating electric field applied during the modulation phase.

14. The method of claim 1, wherein the one or more active ion transporters is a Na/K pump.

15. A system for controlling active ion transporters, the system comprising:

an electric field generator to generate and apply an oscillating electric field to one or more active ion transporters, wherein the oscillating electric field comprises three serially applied phases and applying the oscillating electric field comprises;

applying a synchronization phase to synchronize the active ion transporters to a physiological turnover rate of the active ion transporter down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter sis in a negative half-cycle and the ion-extrusion half-cycle of the active ion transporters is in a positive half-cycle of the oscillating electric field and wherein applying the synchronization phase further comprises:

applying an activation overshoot electric pulse at a start of the negative half-cycle and at a start of the positive half-cycle of the oscillating electric field;

applying an energy-trap overshoot electric pulse at an end of the negative half-cycle and at an end of the positive half-cycle of the oscillating electric field; and         applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and     applying a maintenance phase to maintain the synchronized active ion transporters at the predetermined target turnover rate for a predetermined duration of time.

16. The system of claim 15, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

17. A non-transitory computer-readable medium storing a set of instructions configured for being executed by at least one processor for performing a method for controlling one or more active ion transporters, the method comprising: controlling an electric field generator to apply an oscillating electric field to the one or more active ion transporters, wherein the oscillating electric field comprises three serially applied phases and wherein applying the oscillating electric field comprises;

applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter sis in a negative half-cycle and the ion-extrusion half-cycle of the active ion transporters is in a positive half-cycle of the oscillating electric field and wherein applying the synchronization phase further comprises:

applying an activation overshoot electric pulse at a start of the negative half-cycle and at a start of the positive half-cycle of the oscillating electric field;

applying an energy-trap overshoot electric pulse at an end of the negative half-cycle and at an end of the positive half-cycle of the oscillating electric field; and         applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and     applying a maintenance phase to maintain the synchronized active ion transporters at the predetermined target turnover rate for a predetermined duration of time.

18. The non-transitory media of claim 17, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

* * * * *